(12) United States Patent  
Milijasevic et al.

(10) Patent No.: US 8,182,487 B2
(45) Date of Patent: May 22, 2012

(54) IMPLANTING A TISSUE PROSTHESIS

(76) Inventors: Zoran Milijasevic, Bayview (AU); Ashish Diwan, Sydney (AU)

( * ) Notice: Subject to any disclaimer, the term of this patent is extended or adjusted under 35 U.S.C. 154(b) by 613 days.

(21) Appl. No.: 12/300,112

(22) PCT Filed: May 10, 2007

(86) PCT No.: PCT/AU2007/000626
§ 371 (c)(1),
(2), (4) Date: May 20, 2009

(87) PCT Pub. No.: WO2007/131265
PCT Pub. Date: Nov. 22, 2007

(65) Prior Publication Data
US 2009/0306727 A1    Dec. 10, 2009

Related U.S. Application Data

(60) Provisional application No. 60/747,081, filed on May 11, 2006.

(51) Int. Cl.
*A61B 17/88* (2006.01)
(52) U.S. Cl. .................................. 606/86 A; 623/17.12
(58) Field of Classification Search ................ 606/86 A, 606/99, 192, 914; 623/17.12; *A61B 17/90, A61B 17/88*
See application file for complete search history.

(56) References Cited

U.S. PATENT DOCUMENTS

| | | | |
|---|---|---|---|
| 5,002,556 A * | 3/1991 | Ishida et al. .................. | 606/191 |
| 6,306,177 B1 | 10/2001 | Felt et al. | |
| 6,443,988 B2 | 9/2002 | Felt et al. | |
| 6,969,404 B2 | 11/2005 | Ferree | |
| 7,001,431 B2 | 2/2006 | Bao et al. | |
| 7,025,771 B2 | 4/2006 | Kuslich et al. | |
| 7,077,865 B2 | 7/2006 | Bao et al. | |
| 7,713,301 B2 | 5/2010 | Bao et al. | |
| 7,766,965 B2 | 8/2010 | Bao et al. | |
| 2002/0116009 A1 | 8/2002 | Fraser et al. | |
| 2004/0225295 A1 | 11/2004 | Zubok et al. | |
| 2006/0064107 A1 | 3/2006 | Bertagnoli et al. | |

FOREIGN PATENT DOCUMENTS

| | | |
|---|---|---|
| DE | 3922203 C1 | 10/1990 |
| DE | 202004014119 U1 | 11/2004 |
| WO | WO/02/017825 | 3/2002 |
| WO | WO 03/077808 A2 | 9/2003 |
| WO | WO/2004/073563 | 2/2004 |
| WO | WO 2004/066884 A1 | 8/2004 |

* cited by examiner

*Primary Examiner* — Thomas C. Barrett
*Assistant Examiner* — Christian Sevilla
(74) *Attorney, Agent, or Firm* — Jerry R. Potts

(57) ABSTRACT

A device (12) for implanting a tissue prosthesis comprises an elongate support member (14) having a proximal end (16) and a distal end (13), the support member (14) defining a recessed receiving zone 20 at a distal region for receiving at least a part (22) of the implant in a collapsed configuration. A cover member (24) having a proximal end (26) and a distal end (28) is arranged on the support member (14) to over at least the receiving zone (20) of the support member (14), the cover member (24) being removably arranged relative to the support member (14) to provide access to the receiving zone (20), the cover member (24) and the support member (14) together defining an insertion assembly (32). An insertion formation is defined at the distal end (18) of the insertion assembly (32) for facilitating insertion of at least a distal part of the insertion assembly (32) into position relative to a site in a patient's body in which the implant is to be located, in use, so that, upon removal of the cover member (24), the part (22) of the implant is positioned at the site.

2 Claims, 5 Drawing Sheets

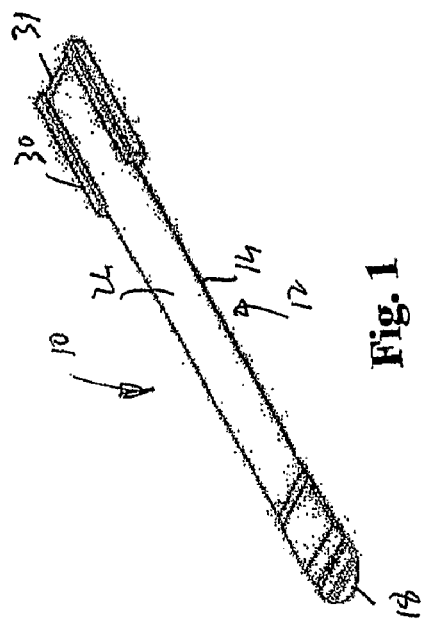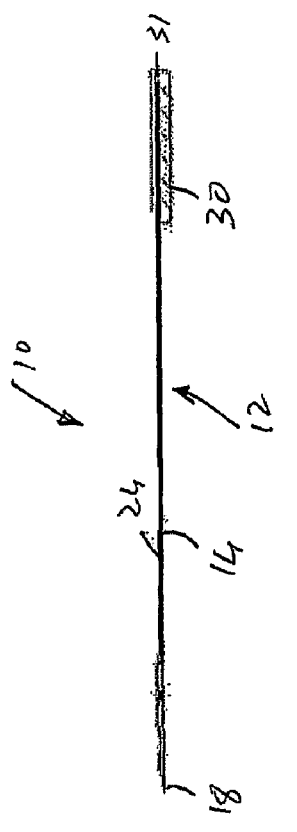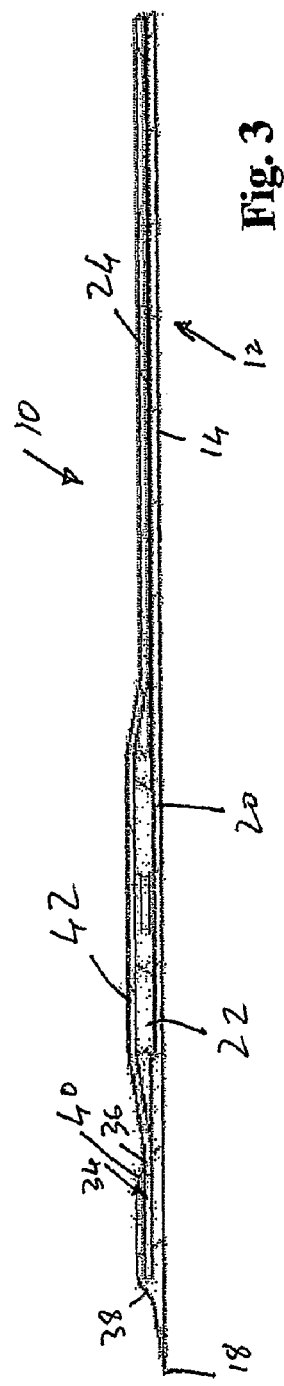

IMPLANTING A TISSUE PROSTHESIS

CROSS-REFERENCE TO RELATED APPLICATIONS

The present application claims priority from U.S. Provisional Patent Application No 60/747,081 filed on 11 May 2006, the contents of which are incorporated herein by reference.

FIELD

This invention relates, generally, to implanting a tissue prosthesis and, more particularly, to a device for implanting a tissue prosthesis and to a system for, and a method of, implanting a tissue prosthesis.

BACKGROUND

In the replacement of degenerative natural tissue with a tissue prosthesis, care needs to be taken to damage surrounding bodily structures as little as possible so as to minimise trauma and to assist in reducing healing time.

An example where a tissue prosthesis is used is in the replacement of a nucleus of an intervertebral disc. An intervertebral disc comprises two parts, an annulus fibrosis surrounding a nucleus pulposus or nucleus. The intervertebral disc cooperates with end plates of the vertebrae between which it is sandwiched.

Various techniques have been proposed for dealing with age or injury related intervertebral disc degeneration. Two techniques in use are disc removal and fusion. Both of these techniques involve major invasive surgery with the related risks. More recently, another technique employed has involved the replacing of a degenerative disc with an artificial disc. This, once again, is carried out using major invasive techniques. Still more recently, techniques have been proposed to replace only the nucleus of the disc in circumstances where the degeneration is detected at a sufficiently early stage. Such techniques may be able to be performed in a minimally invasive manner.

A need exists when doing minimally invasive replacement of degenerative tissue with a prosthesis to cause as little trauma to surrounding bodily structures of the disc as possible.

SUMMARY

According to a first aspect of the invention, there is provided a device for implanting a tissue prosthesis, the device comprising an elongate support member having a proximal end and a distal end, the support member defining a receiving zone at a distal region for receiving at least a part of the implant in an at least partially collapsed configuration;

a cover member having a proximal end and a distal end arranged on the support member to cover at least the receiving zone of the support member, the cover member being removably arranged relative to the support member to provide access to the receiving zone, the cover member and the support member together defining an insertion assembly; and an insertion formation defined at the distal end of the insertion assembly for facilitating insertion of at least a distal part of the insertion assembly into position relative to a site in a patient's body in which the implant is to be located, in use, so that, upon removal of the cover member, the at least part of the implant is positioned at the site.

The part of the implant may be an expandable element, or envelope, one of the support member and the cover member defining a receiving formation within which a filler conduit is receivable.

The receiving zone may be a recess defined at the distal region of the support member, the recess being dimensioned to accommodate at least a part of the envelope in an at least partially collapsed configuration. The receiving formation may be a channel defined in the support member, a distal end of the channel opening out into the recess.

The support member and the cover member may carry complementary locating formations at their distal ends for locating the support member and the cover member relative to each other for insertion into the patient's body. For example, the support member may have a proximally facing, transversely extending slot defined at its distal end. The cover member may have a distally extending tab or tongue arranged its distal end to be received in the slot.

The cover member may include a raised formation received over the recess when the cover member is positioned on the support member, the raised formation being arranged proximally of the locating formation of the cover member. The raised formation may be an arched part arranged at a distal region of the cover member to accommodate the collapsed envelope beneath it and to retain the envelope in the receiving zone of the support member.

The support member and the cover member may be substantially flat to facilitate insertion of the insertion assembly into position at the site. For example, in the case of the application of the invention in the replacement of a nucleus of an intervertebral disc, the insertion assembly may be inserted between the disc and an adjacent vertebra end plate.

The insertion formation may be a spatulate tip arranged at a distal end of the support member. The distal end of the support member may be ramped proximally of the spatulate tip to facilitate insertion and removal of the support member.

The device may include a retaining member which engages the support member and the cover member to retain the support member and the cover member in position relative to each other and to facilitate insertion of the insertion assembly into the patient's body.

According to a second aspect of the invention, there is provided a system for implanting a tissue prosthesis, the system including a spatulate introducer which is dimensioned to be introduced between two bodily structures of a patient's body;

an expandable envelope received in an at least partially collapsed configuration in a receiving zone defined at a distal region of the introducer; and a filler conduit connected to the expandable envelope to communicate with an interior of the envelope.

The introducer may comprise at least two parts, a support member defining the receiving zone and a cover member for covering the collapsed envelope received in the receiving zone.

At least one of the support member and the cover member may have a spatulate tip for facilitating introduction of the introducer between the bodily structures, for example, a disc and an adjacent vertebra.

The filler conduit may be releasably connected to the envelope. The envelope may include a filler opening to which the filler conduit is connected, the envelope further including a closure member associated with the filler opening, the closure member closing off the opening after charging of the envelope with filler material has been completed.

The envelope may be of a biocompatible elastomeric material. For example, the elastomeric material may be a silicone material having an elongation of up to about 1000%

The system may include a source of filler material for effecting expansion of the implant in situ within the patient's body. The filler material may be an elastomeric filler material which is able to be injected into the envelope to cure in situ. Once again, the filler material may be a silicone material so that, when the filler material has been charged into the envelope and has set, a homogeneous, elastically deformable structure is formed.

According to a third aspect of the invention, there is provided a method of implanting a tissue prosthesis, the method including mounting an expandable envelope, in an at least partially collapsed configuration, on a spatulate introducer;

inserting the introducer between two bodily structures of a patient's body;

charging a filler material into the expandable envelope; and extracting the introducer from between the two bodily structures.

The introducer may comprise at least two parts, being a support member and a cover member and the method may include placing the envelope, in its at least partially collapsed configuration, into a receiving zone defined at a distal region of the support member and covering the collapsed envelope with the cover member prior to inserting the introducer into position between the two bodily structures.

The method may include, prior to inserting the introducer into position, performing a procedure to form a volume defined at least partially by the two bodily structures to be filled by the implant in its expanded configuration.

The method may include removing the cover member once the envelope has been positioned within the volume.

Further, the method may include charging the filler material into the envelope to cause the envelope to expand to conform to the volume.

The method may include removing the support member from its position between the two bodily structures and removing a filler conduit, via which the filler material was charged into the envelope, from the envelope and allowing the filler material to cure.

BRIEF DESCRIPTION OF DRAWINGS

FIG. 1 shows a schematic, three dimensional view of a system, in accordance with an embodiment of the invention, for implanting a tissue prosthesis;

FIG. 2 shows a sectional side view of the system;

FIG. 3 shows, on an enlarged scale, a sectional side view of a distal part of the system;

DETAILED DESCRIPTION OF EXEMPLARY EMBODIMENT

Figure 4:
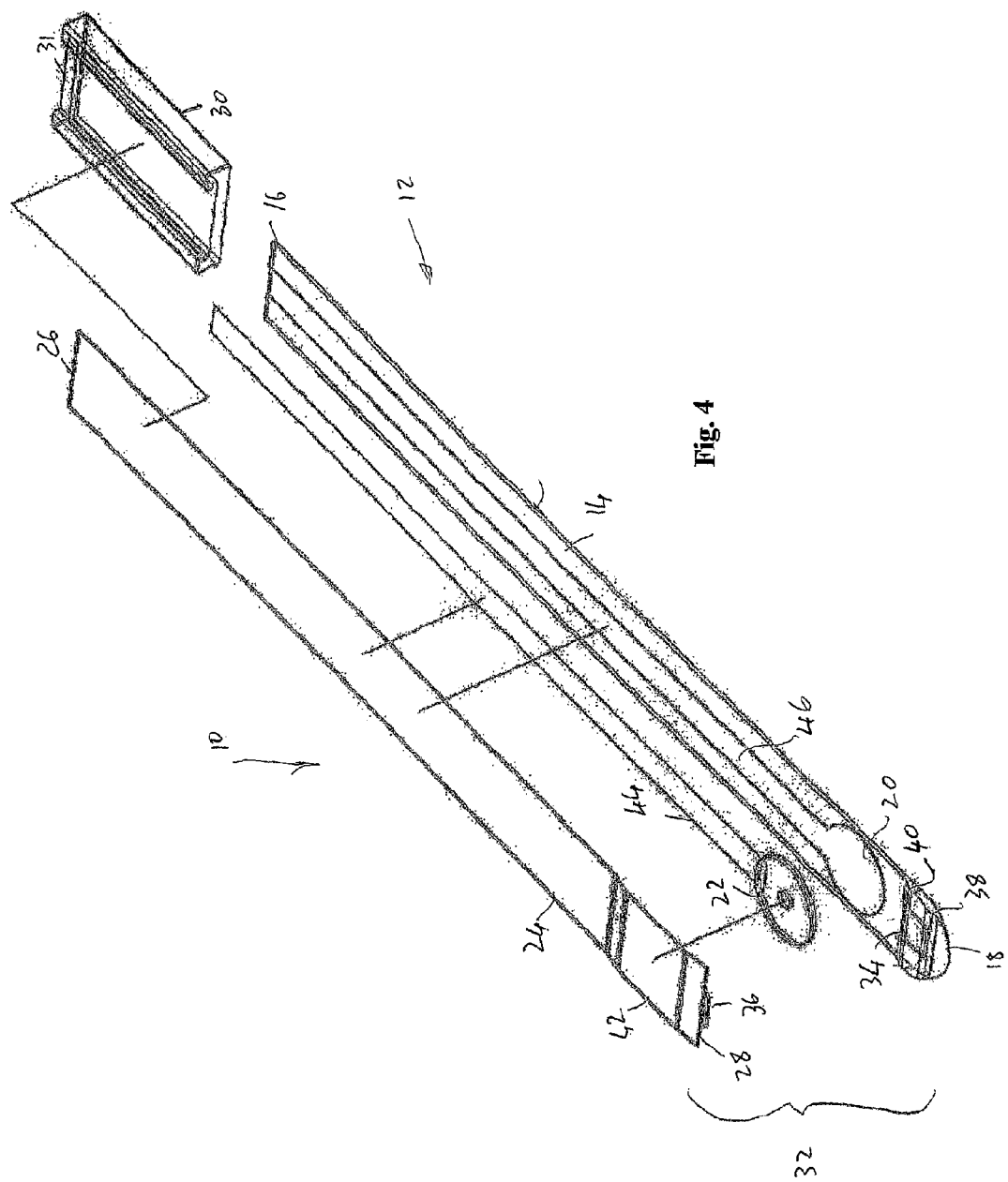
FIG. 4 shows a three dimensional, exploded view of the system.
Figure 5:
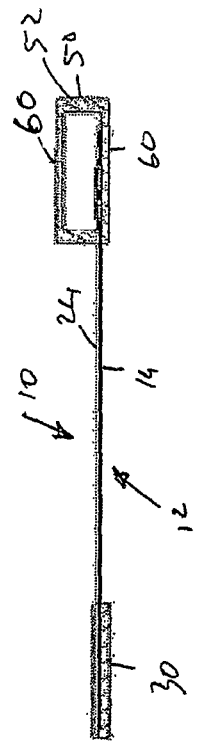
FIG. 5 shows a schematic, sectional side view of the system, in use.
Figure 6:
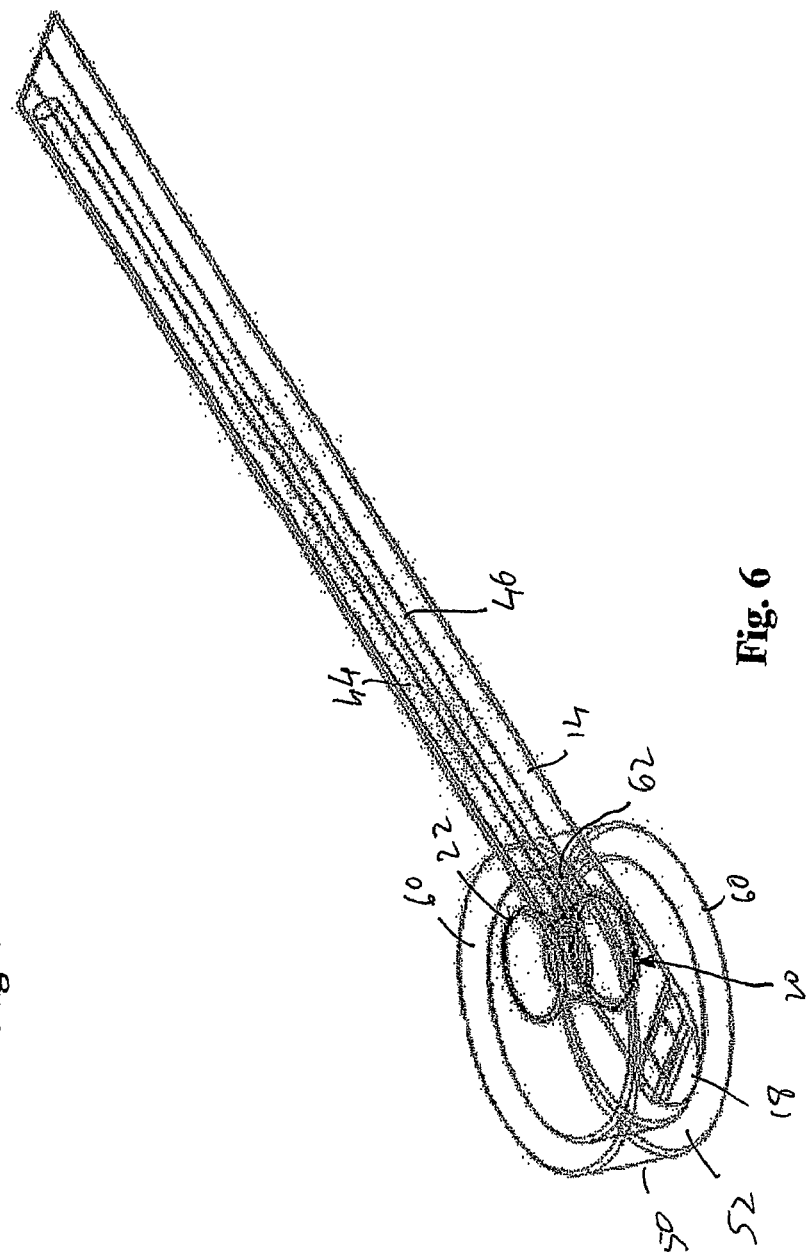
FIG. 6 shows a schematic, three dimensional view of a part of the system, in use.

In the drawings, reference numeral 10 generally designates a system, in accordance with an embodiment of the invention, for implanting a tissue prosthesis. The system 10 includes a device 12, also in accordance with an embodiment of the invention, for implanting the prosthesis. The invention has particular, but not necessarily exclusive, application in implanting an intervertebral disc prosthesis within a disc. For ease of explanation, the invention will be described with reference to its application in implanting an intervertebral disc prosthesis within a disc.

The device 12 includes an elongate, substantially flat support member 14 having a proximal end 16 (FIG. 4) and a spatulate, distal end 18. The support member 14 defines a receiving zone in the form of a recess 20 proximally of the distal end 18. An expandable envelope 22 of an intervertebral disc prosthesis is received, in a collapsed configuration, within the recess 20. Thus, the recess 20 is shaped and dimensioned such that the envelope 22, when in its collapsed configuration, is a snug fit within the recess 20.

The device 12 further includes a cover member 24. The cover member 24 has a proximal end 26 and a distal end 28. The cover member 24 is shaped and dimensioned to be received over the support member 14 and is also substantially flat and has substantially the same width as that of the support member 14. Both the support member 14 and the cover member 24 are of a bio-compatible material, for example, surgical steel.

The device 12 further includes a retaining member in the form of a slide 30. The slide 30 receives the proximal ends 16 and 26 of the support member 14 and the cover member 24, respectively, when the cover member 24 is placed over the support member 14. The slide 30 retains the cover member 24 in position relative to the support member 14. Further, the slide 30 facilitates insertion of an insertion assembly 32, comprising the support member 14 and the cover member 24, into a patient's body, as will be described in greater detail below. The slide 30 has a raised lip 31 at its proximal end against which the proximal ends 16 and 26 of the support member 14 and the cover member 24, respectively, abut in use to limit displacement of the slide 30 distally.

The distal ends 18 and 28 of the support member 14 and the cover member 24 carry complementary locating formations 34 and 36, respectively.

The distal end 18 of the support member 14 is spatulate to facilitate insertion of the distal part of the insertion assembly 32 into position relative to the disc, as will be described in greater detail below. Forwardly and rearwardly extending ramped formations 38 and 40, respectively, are defined proximally of the distal end 18 of the support member 14. The purpose of the ramped formations 38 and 40 is to facilitate insertion of the distal part of the insertion assembly 32 into position relative to the disc and removal of the distal part of the support member 14 from within the disc.

The locating formation 34 of the support member 14 comprises a slot opening out, in a proximal direction, into the ramped formation 40. The locating formation 36 of the cover member 24 is in the form of a distally extending tab which is received in the slot 34 of the support member 14 for retaining the cover member 24 in position relative to the support member 14, in use.

The distal end 28 of the cover member 24 has a raised, bowed or arched, formation 42 to accommodate the envelope 22. The arched formation 42 also facilitates placement of the envelope 22 in position in the disc and removal of the distal part of the cover member 24 from within the disc.

As described above, the envelope 22 is expandable. A filler conduit, in the form of a filler tube, 44 communicates with an interior of the envelope 22. The support member 14 defines a receiving formation, in the form of a channel, 46 within which the filler tube 44, in a deflated condition, is received. The filler tube 44 releasably attaches to a filler opening 45 (FIG. 7) of the envelope 22.

Typically, the expandable envelope 22 is of an elastomeric material which has an elongation of up to about 1000% and, more particularly, is of a silicone material. As described in the Applicant's co-pending U.S. Provisional Patent Application No. 60/708,670 dated 15 Aug. 2005, entitled "A tissue prosthesis and a method of, and equipment for, forming a tissue prosthesis", the envelope 22 is filled with a material of the same characteristic to form the prosthesis. Thus, the envelope 22, in use, is filled with an elastomeric, more particularly, a silicone material, to form a homogeneous, elastically deformable disc nucleus prosthesis.

In use, the expandable envelope 22 with its filler tube 44 is placed in position on the support member 14. More particularly, the envelope 22 is received in the recess 20 while the envelope 22 is in a collapsed configuration. The filler tube 44, similarly in a deflated condition, is received in the channel 46 of the support member 14.

The cover member 24 is placed over the support member 14 by inserting the tab 36 into the slot 34 of the support member 14 to form the insertion assembly 32. The proximal ends 16 and 26 of the support member 14 and the cover member 24, respectively, are held in position by the slide 30 being received over the proximal ends of the insertion assembly 32. To assist in subsequent removal of the cover member 24 from the support member 14 later in the procedure, an inner surface of the cover member 24 and/or the support member 14 is coated with a lubricant, such as water or a hygroscopic or hydrophobic material, for example, a hydrogel, before placing the cover member 24 on the support member 14.

Figure 10:
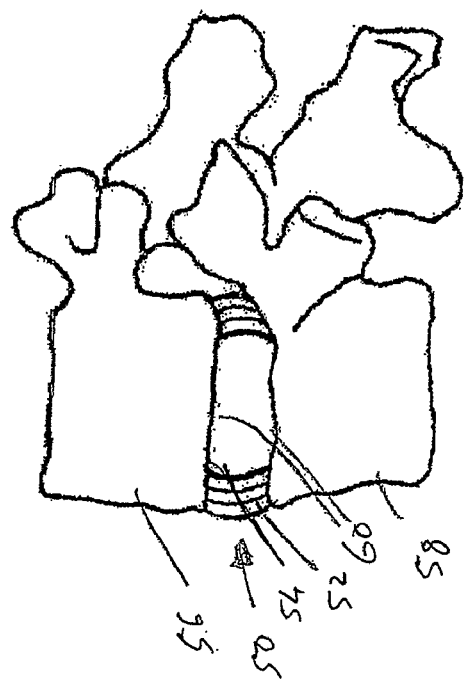
FIG. 10 shows a side view of a part of a person's spine.
Figure 9:
FIG. 9 shows a sectional side view of the envelope.
Figure 8:
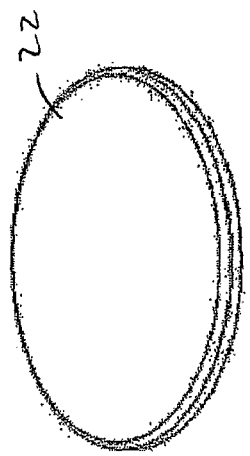
FIG. 8 shows a three dimensional view of an expandable envelope of an implant of the system.

As described above, an intervertebral disc 50, as shown in FIG. 10 of the drawings, comprises an annulus fibrosis 52 and a nucleus pulposus 54. The disc 50 is located between adjacent vertebrae 56, 58. Each vertebra 56, 58 defines an end plate 60 which, together, cooperate to control ingress of nutrients into the disc 50 and expulsion of waste material from within the disc 50.

In the case of a degenerative disc 50, herniation or other damage to the annulus fibrosis 52 may cause escape of the nuclear material of the nucleus pulposus 54 from within the disc 50. Herniation of the disc 50 can cause severe discomfort to the patient and in order to alleviate this discomfort it is necessary to perform an operation on the degenerative disc 50. Ideally, if the diseased disc 50 is detected at a sufficiently early stage of degeneration, it may be possible to alleviate the symptoms by replacing the damaged nucleus pulposus 54 of the disc 50 by an artificial prosthesis of which the envelope 22 forms a part.

Thus, initially, the disc 50 is accessed percutaneously by making an incision through the patient's skin. A small incision 62 is made in the annulus fibrosis, as close to the junction between the annulus fibrosis and one of the end plates 60, for example, the end plate of the vertebra 58. Depending on the degree of degeneration of the nucleus pulposus 54, a nucleotomy may or may not be performed. If there is insufficient space within the disc 50, a nucleotomy is performed via the incision 62 in the annulus fibrosis 52 and removing the nuclear material. A device such as a reaming tool (not shown) is inserted into the interior of the disc through the incision 62 and the nuclear material is removed. If, however, the degeneration is sufficiently advanced that most of the nuclear material has escaped from within the annulus fibrosis, it may not be necessary to perform the nucleotomy. In that case, the implant may merely be positioned in the disc through the incision without the need for a nucleotomy.

The spatulate distal end 18 of the support member 14 of the insertion assembly 32 is inserted through the incision in the patient's skin into position between the edge of the annulus fibrosis 52 and the end plate 60 of the vertebra 58 adjacent the incision 62. The spatulate end 18 is urged between the annulus fibrosis 52 and the end plate 60 through the incision so that the arched formation 42 of the cover member 24 is within the volume created by the absence of nuclear material within the disc 50.

The slide 30 is removed from the proximal end of the insertion assembly 32. Once the slide 30 has been removed, the cover member 24 itself is removed to expose the envelope 22. For this purpose, the arched formation 42 assists in removal of the distal part of the cover member from within the disc 50.

Figure 7:
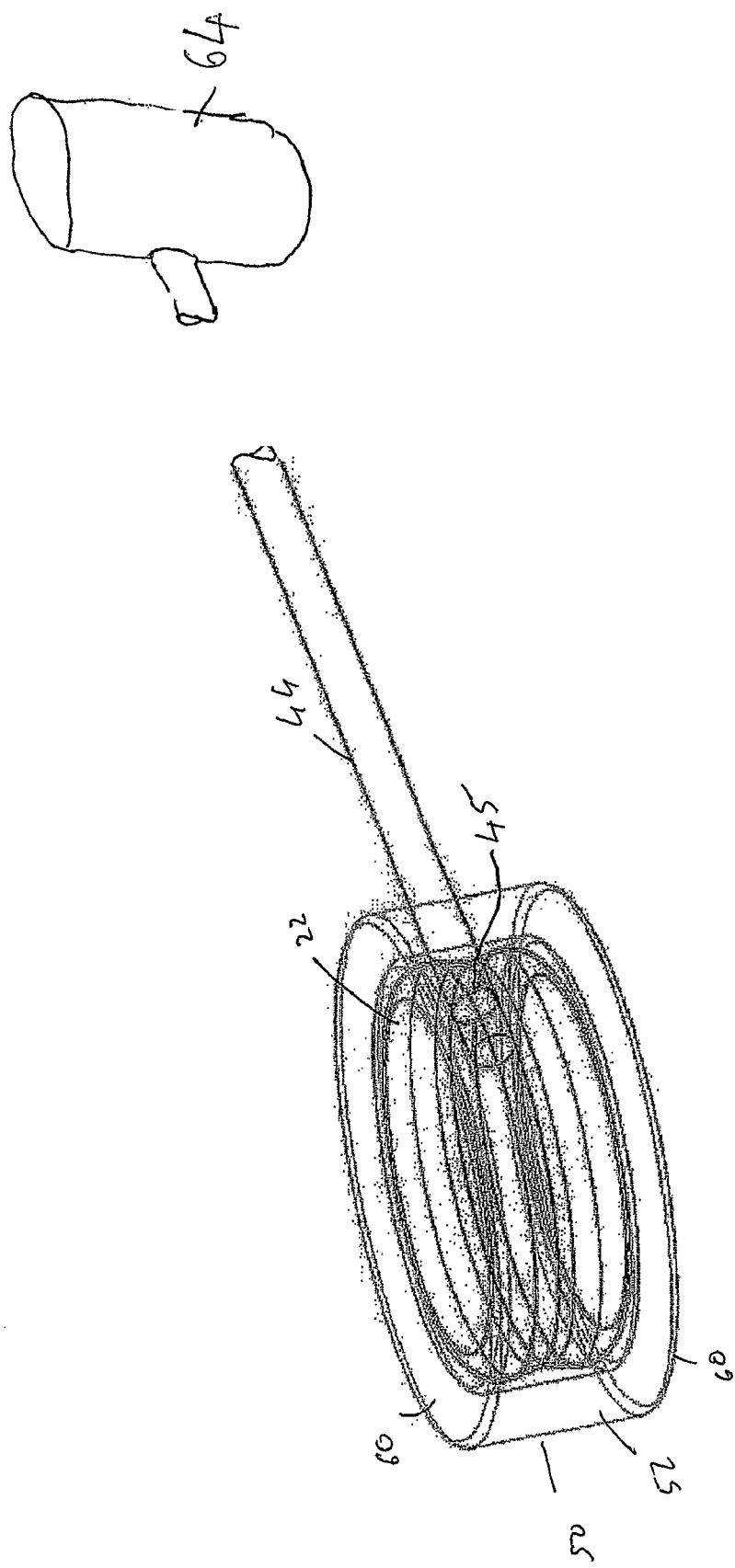
FIG. 7 shows a schematic, three dimensional view of a part of the system, in use.

A proximal end of the filler tube 44 is attached to a reservoir 64 of filler material. The filler tube 44 is arranged within the incision 62 so that it is able to expand. The filler material is charged through the filler tube 44 into the envelope 22 to cause the envelope to expand as shown in FIG. 7 of the drawings. The envelope 22 is charged with filler material until it conforms substantially to the volume of the disc 50. In fact, the envelope 22 is slightly over expanded while the support member 14 is in position.

Once the envelope 22 has been expanded to its desired pressure or size, the filler tube 44 is detached from the envelope 22. A non-return valve (not shown), such as a duck bill valve, arranged within the interior of the envelope 22 closes off the filler opening 45 of the envelope 22 to inhibit escape of filler material.

The support member 14 is then removed and, for this purpose, the ramped formation 40 assists in removal of the distal part of the support member 14 from within the interior of the disc 50. Because the envelope 22 had previously been slightly over expanded, removal of the support member 14 allows the envelope 22 more fully to conform to the volume of the disc 50. The expanded envelope 22 functions as an artificial nucleus pulposus of the disc 50 and the prosthesis functions in a similar biomechanical manner to a natural nucleus pulposus.

Because the annulus fibrosis 52 of the disc 50 is made up of meshing collagen fibres, the Applicants believe that, in due course, the incision 62 made to accommodate the filler tube 44 will self heal, i.e. will close. In this regard, there is evidence to suggest that the annulus fibrosis 52 heals better to vertebral matter than it does to annular matter itself. In other words, an incision made at the junction between the annulus fibrosis and the vertebral end plate should heal better than an incision into the annular fibrosis itself.

It is an advantage of the invention that a system 10 and device 12 are provided which minimally affects the bodily structures such as an annulus fibrosis of an intervertebral disc on which a minimally invasive procedure is being carried out. The shape of the distal part of the device 12 facilitates its placement between bodily structures and also the removal of the components of the device post-placement of the implant.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A system for implanting an intervertebral prosthesis, the system comprising:

an elongate support member being substantially flat throughout its entire longitudinal length having a proximal end, a distal end, an upper surface and a lower surface;

a recess disposed in said upper surface proximally of said distal end, said recess being shaped and dimensioned for receiving substantially therein and for supporting from below a substantially flat collapsed expandable envelope for helping to form the intervertebral prosthesis;

an elongate cover member being substantially flat throughout its entire longitudinal length having a proximal end and a distal end, said cover member being shaped and dimensioned to be received on said support member;

said cover member arranged on the support member to cover at least the recess, said cover member being removably arranged relative to the support member to provide access to said recess;

an arched formation disposed proximally of the distal end of said cover member to help provide sufficient space between said support member and said cover member for said substantially flat collapsed expandable envelope when said envelope is disposed in said recess;

forwardly and rearwardly extending ramped formations disposed proximally of the distal end of said support member for facilitating insertion of at least a distal part of said support member and said cover member into position relative to an implant site for said envelope;

wherein said forwardly extending ramped formation tapers and decreases in thickness towards the distal end of said support member;

wherein said rearwardly extending ramped formation tapers and decreases in thickness towards the proximal end of said support member;

wherein said recess opens out into an elongated channel disposed in said upper surface;

wherein said channel extends from the proximal end of said upper surface to a proximal portion of said recess;

wherein the support member and the cover member carry complementary locating formations for locating the support member and the cover member relative to each other for insertion into the patient's body, the locating formations comprising a slot opening out into the rearwardly extending ramped formation and a tab extending from the cover member into said slot;

wherein said envelope is positioned in said recess; and wherein a tube is positioned in said channel, said tube being in fluid communication with said envelope.

2. The device of claim 1 in which the support member has a spatulate tip arranged at a distal end thereof.

\* \* \* \* \*